US009241802B2

(12) United States Patent
Klawitter et al.

(10) Patent No.: US 9,241,802 B2
(45) Date of Patent: Jan. 26, 2016

(54) HUMERAL HEAD RESURFACING IMPLANT

(71) Applicant: Ascension Orthopedics, Inc., Austin, TX (US)

(72) Inventors: Jerome J. Klawitter, Austin, TX (US); Robert B. More, Austin, TX (US); Monti R. Gourley, Austin, TX (US); Joseph P. Ritz, San Antonio, TX (US); Evgeny G. Podnos, Austin, TX (US)

(73) Assignee: Ascension Orthopedics, Inc., Austin, TX (US)

( * ) Notice: Subject to any disclaimer, the term of this patent is extended or adjusted under 35 U.S.C. 154(b) by 0 days.

(21) Appl. No.: 14/246,457

(22) Filed: Apr. 7, 2014

(65) Prior Publication Data

US 2014/0222154 A1    Aug. 7, 2014

Related U.S. Application Data

(63) Continuation of application No. 13/523,012, filed on Jun. 14, 2012, now Pat. No. 8,690,958.

(51) Int. Cl.
*A61F 2/40* (2006.01)
*A61F 2/30* (2006.01)

(52) U.S. Cl.
CPC ............. *A61F 2/4014* (2013.01); *A61F 2/4003* (2013.01); *A61F 2002/30112* (2013.01); *A61F 2002/30884* (2013.01); *A61F 2002/4007* (2013.01); *A61F 2002/4022* (2013.01); *A61F 2310/00173* (2013.01); *A61F 2310/00574* (2013.01)

(58) Field of Classification Search
CPC .............................. A61F 2/4014; A61F 2/4003
See application file for complete search history.

(56) References Cited

U.S. PATENT DOCUMENTS

| | | | | |
|---|---|---|---|---|
| 5,677,061 | A * | 10/1997 | Ely et al. ........................ | 428/408 |
| 2004/0225367 | A1 * | 11/2004 | Glien et al. ................. | 623/19.14 |
| 2007/0156250 | A1 * | 7/2007 | Seitz et al. .................. | 623/23.51 |
| 2009/0143865 | A1 * | 6/2009 | Hassler et al. ............. | 623/19.11 |
| 2011/0054631 | A1 * | 3/2011 | Ratron et al. .............. | 623/23.12 |

* cited by examiner

*Primary Examiner* — Bruce E Snow
*Assistant Examiner* — Melissa Hoban
(74) *Attorney, Agent, or Firm* — Eva Tan

(57) ABSTRACT

A humeral head resurfacing implant (11) that has a modulus of elasticity close to that of human cortical bone as a result of its design from an integral substrate of isotropic graphite covered completely with a reinforcing layer of dense isotropic pyrolytic carbon. A carefully engineered cruciform stem (15) extends from the axial center of a flat distal circular surface (23) of a spherical cap portion (19) of the implant head located within the confines of a surrounding skirt portion (21).

14 Claims, 2 Drawing Sheets

HUMERAL HEAD RESURFACING IMPLANT

This application is a continuation of U.S. application Ser. No. 13/523,012 filed Jun. 14, 2012, now U.S. Pat. No. 8,690,958, which is a continuation of international Application No. PCT/US2010/059301, filed Dec. 7, 2010, which claims priority from U.S. Provisional Application Ser. No. 61/286,284 filed Dec. 14, 2009, the disclosures of all of which are incorporated herein by reference.

This invention relates to a prosthetic implant designed to function as a humeral head resurfacing prosthesis. More particularly, it relates to a humeral head resurfacing implant having an improved design that enhances stem strength and stem fixation to bone while conserving bone stock and providing overall bone and cartilage compatibility.

BACKGROUND OF INVENTION

Humeral Head Arthroplasty

Disease and injury often require shoulder joint arthroplasty using a humeral head prosthesis. There are two types of humeral head prostheses in general use; one is a humeral head resurfacing implant and the other a humeral head replacement implant. Humeral head resurfacing is a conservative approach to humeral head arthroplasty and is usually accomplished by using a thin-wall, dome-shaped shell to resurface the humeral head. The resurfacing implant has a central stem that is placed in the humeral neck following bone preparation to achieve fixation to the humeral bone. In humeral head replacement, the entire humeral head is cut off during surgery, and the humeral head replacement implant has a long medullary stem to fix the implant to the humeral bone.

The shoulder joint is formed by the head of the humerus articulating with a shallow socket called the glenoid. The glenoid is located on the lateral margin of the scapula. Humeral head resurfacing and replacement implants can be total joint implants or hemi-joint implants. Total joint implants typically have a polyethylene socket component that replaces the glenoid avid articulates with a humeral head replacement.

More than half of the shoulder joint arthroplasty presently done in the US are hemi-arthroplasty because exposure to provide access to the glenoid is difficult. The bone mass comprising the glenoid is limited, and because of this, glenoid replacement components often loosen. For hemi-arthroplasty, humeral head replacement, may be presently more commonly used than humeral head resurfacing.

A humeral head resurfacing implant was developed by Dr. S. A. Copeland and was first used clinically in about 1986. The Copeland implant consists of a thin-wall, metal, spherical, dome-shaped shell having a central tapered and flirted, stem intended to achieve fixation of the implant to bone.

Humeral head resurfacing arthroplasty has the following benefits when compared to humeral head replacement.

1. Humeral head resurfacing is a conservative procedure requiring much less removal of bone than humeral head replacement. In humeral head replacement, the entire humeral head is removed, and a substantial amount of bone is also removed to make room for the long medullary stem that extends deep into the proximal shaft of the humerus. In humeral head resurfacing, only articular cartilage and a small amount of the subchondral bone is removed from the humeral head to reshape it for reception of the resurfacing implant. In like manner, only a small amount of bone is removed from the humeral head to make room for the implant stem. Minimal bone removal is an objective and a benefit of humeral head resurfacing. The humeral head is left essentially intact during the resurfacing procedure; such maintains the integrity and strength of the humeral head bone structure. Maintaining integrity and strength of the humeral head bone is important because the native humeral head structure provides the foundation needed to support the biomechanical loads that will be encountered by the humeral head resurfacing implant.

2. The orientation of the humeral head with respect to the long axis of the humerus varies considerably from, individual to individual. With humeral head replacement, many combinations of head and stem components having different shapes are required to achieve the correct anatomic position of the humeral head for each individual patient. With humeral head resurfacing the position and location of the humeral head is not altered during surgery and the individual anatomy of each patient is preserved.

3. Substantial intra-medullary reaming is not required. Therefore, this is a less traumatic procedure in an elderly patient that reduces risk of fat embolus or hypotension.

4. If there is malunion (non-healed fracture) at the proximal end of the humeral with secondary osteoarthritis, the malunion can be left undisturbed and just the humeral articular surface replaced.

5. With humeral head resurfacing, there is no stem extending down the humeral shaft, and therefore no possibility of humeral shaft bone loss due to stress shielding or a stress riser effect that could result, in a low fracture at the tip of the prosthesis.

Humeral Head Resurfacing Surgical Procedure

The surgical procedure consists of making a surgical incision that provides access to the glenohumeral joint so that the shoulder can be dislocated and the humeral head exposed. Once exposed, the size and shape of the humeral head can be determined and an appropriate size implant selected. A guide pin is then placed into the humeral head which serves to orient a cutting instrument that reshapes the humeral head to conform to the concave inner surface of the implant. Following reshaping of the humeral head, a cannulated cutting tool is place over the guide pin and used to form the cavity into which the implant stem will be placed. The resurfacing implant is then placed onto die previously prepared humeral head, and an inspector is then used to firmly seat the implant in bone resulting in a press fit. A radiograph is then taken to confirm the implant is properly placed.

Contact of the inner concave surface of the dome-shaped implant head portion with the surgically prepared convex mating bone surface of the humeral head provides a large load-bearing area to support joint contact loads. Because the contact between the concave inner surface of the implant and the convex outer surface of the humeral head will not resist rotation of the implant along multiple axes, the implant generally relies upon its stem to resist rotation.

Regarding the implant stem, there are two design options. One is a mono-body configuration, i.e. a single unit where the stem is an integral part of the implant; the other is a modular configuration where stem components of various sizes can be attached to shell components of various sizes. Modular designs are often used for orthopedic joint replacements as a means to accommodate variations in anatomy from one individual to another. However, a modular design necessarily requires a secure means of attaching the stem component to the head component of the device, which is most often accomplished using a taper locking system (e.g. cone-in-cone Morse taper). A locking taper inherently requires that additional material to be used to form the implant stem or inner portion of the shell to form the female component of the cone-in-cone connection. The structure necessary for the female portion of the locking taper takes up additional space, and it requires more bone to be removed as compared to a similar mono-body design. Moreover, the need for removal, of the additional bone required for such a taper lock modular design violates the objective of the resurfacing design principle, namely minimal bone removal, and as a result, it reduces the load-bearing capacity of the surgically modified humeral head. Thus, for a humeral head resurfacing implant, a one-piece mono-body configuration that will require substantially less bone removal should be the preferred design.

Humeral Head Resurfacing Implant Fixation

Long Term Fixation

Fixation of the humeral head resurfacing implant to bone can be achieved using bone cement or by means of material capable of achieving biological fixation. Bone cement is known to cause chemical and thermal bone damage during insertion resulting bone necrosis and is known to fracture and fragment while in situ. Both of these factors can result in loss of implant fixation. Biological fixation, where living bone attaches permanently to the implant surface, is considered an advantageous alternative to bone-cement fixation. Biocompatible materials, such as titanium, that allow direct bone to implant adaptation resulting in osseous integration, and porous material coatings that allow for bone ingrowth and hydroxyapatite (HA) coatings that result in a bone to HA bond are means of achieving biological attachment. Biological attachment relies on the bone's natural healing ability to achieve fixation of the implant.

Primary Fixation

Achieving long term stable biological fixation of implant requires time for the bone healing process to integrate, grow into or hood bone to the implant stem. In this regard, achieving biological fixation of implant to bone is similar in principle to the healing of a fractured bone. Following a fracture, a biologic response generates new bone to bridge the fracture and unite the pieces of the fractured bone. During the fracture healing process, it is necessary that the ends of the fractured bone are immobile. Immobilizing fracture bones is accomplished clinically by applying an external cast or using internal fixation devices such a plates and screws, wires or intramedullary rods. If the fracture fragments are not adequately immobilized during the 6-8 weeks necessary for fracture healing, it is likely the fracture will not heal, resulting in a non-union (malunion). A requirement for 6-8 weeks of immobilization to achieve fracture healing following surgery also applies to achieving biological fixation of an implant. The implant must be immobile to allow the bone tissue to integrate, grow into and or bond to the implant stem, if the implant is not immobile during the post-operative healing period it is likely a secure biological attachment of implant to bone will not be achieved.

In the case of a humeral head resurfacing implant it is the stem of the implant that provides the primary fixation required to achieve biological attachment. The implant stem most be designed to provide adequate post-operative immobilization for a period of 6 8 weeks so that biological fixation of the implant stem to bone can be achieved.

Humeral Head Resurfacing Implants in Current Use

Two humeral head resurfacing devices are in common use at this time, one produced by Biomet Orthopedics (Copeland implant) and the other produced by DePuy Orthopedics (Global C. A. P, implant).

The Biomet Copeland humeral head resurfacing implant is a mono-body device consisting of a dome-shaped shell having a spherical convex outer articular surface, a concave inner surface and a central peg shaped stem to achieve fixation in the humeral bone. The device is made of ASTM F-75 Co—Cr casting alloy, and the outer convex surface is polished and intended to act as the articulating surface. The inner concave surface is intended to bear against the surgically prepared humeral head. A tapered, four fluted stem extends outward from the center on the inner concave surface of the shell. The stem is inserted into a surgically created cavity made in the humeral head and is intended to stabilize the device in the humeral bone. The inner concave surface of the dome-shaped shell has a plasma-sprayed titanium layer to achieve osseous integration and is available with a plasma-sprayed hydroxyapatite (HA) layer placed on the titanium layer to promote bonding of the implant to bone. The Copeland Humeral Head Resurfacing Implant is approved for use with and without bone-cement.

The DePuy C.A.P. humeral head resurfacing implant is a mono-body device consisting of a dome-shaped shell having a spherical convex outer articular surface, a concave inner surface and a central peg shaped stem to achieve fixation in the humeral bone. The device is made of ASTM F-75 Co—Cr casting alloy, and the outer convex dome surface is polished to act as the articulating surface. The inner concave dome surface has a porous Co—Cr alloy layer intended to bear against the surgically prepared humeral head. The tapered stem has a frusto-conical upper section that extends outward from the center of the inner concave surface of the dome and a cruciate lower section. The innermost surface of the concave dome where the stem connects to the dome is flat; that is, the concave portion of the dome has the shape of a truncated sphere. A porous coating on the stem extends approximately one half-way down the stem of the implant. The distal portion of the stem has four flutes providing rotational stability to the implant. The stem is inserted into a surgically created cavity made in the humeral head and is intended to stabilize the device in the humeral bone. As an added feature to enhance fixation, the C.A.P. implant can be obtained with a hydroxyapatite (HA) coating placed on the porous Co—Cr layer. The DePuy C.A.P. Humeral Head Resurfacing Implant is approved for use with and without bone-cement.

Despite the tact that there are various humeral head resurfacing implants on the market in the United States at the present time, none of them is considered to be totally satisfactory. Other examples of humeral head resurfacing implants are found in U.S. Pat. Nos. 4,520,964; 6,783,549; and 7,517,364 and in Published Application. Nos. 2006/0009852, 2007/0156250, 2007/0225822 and 2008/0021564. The humeral head components of these implants (both for humeral head replacement and resurfacing) in commercial use today in total and hemi-joint replacement are generally made of Co—Cr alloy. It is recognized that Co—Cr alloy is damaging to joint tissues (cartilage and bone), and this is a shortcoming of such hemi-arthroplasty devices. However, from an overall standpoint, Co—Cr alloy has become the material of present choice. Pyrolytic carbon (pyrocarbon) has been shown to be much less damaging to native joint tissues (cartilage and bone); thus, it would be a better material for hemi-arthroplasty than either metal or ceramics such as aluminum oxide or zirconia. However, pyrolytic carbon has significantly different properties, and as a result has generally achieved commercial use primarily on articular surfaces.

Accordingly, improvements in such resurfacing implants continue to be sought, particularly ones that would utilize pyrocarbon.

SUMMARY OF THE INVENTION

The invention provides a humeral head resurfacing implant formed of specific materials and having an improved interior/stem construction, which utilizes a cruciform cross-sectional geometry, that provides both adequate stem strength and stem surface area without removing excessive amounts of bone; this implant excellently achieves primary and long term fixation to the resurfaced humerus and provides the benefits of pyrocarbon. The stem basically employs four fins that extend radially outward in cruciform shape from a center axial region and which are shaped and proportioned to achieve the desired objective of providing adequate strength in a graphite-pyrocarbon structure while requiring only minimum removal of bone material. The interior construction allows fin thickness to be minimized while assuring adequate strength in regions of joinder between the stem and the head or cap.

In a particular aspect, the invention provides a humeral head resurfacing implant comprising an integral head and stem which includes: an integral isotropic graphite substrate having a head portion and a stem portion of cruciform cross section which extends distally therefrom, a coating of dense isotropic pyrocarbon having a thickness of at least about 0.2 mm that covers substantially said entire substrate, which pyrocarbon has a density of between about 1.7 and 2.1 gm/cm$^3$ and a hardness of at least about 200 DPH, said head having an exterior surface shape of a section of a spheroid which serves as a proximal surface to interface with a patient's glenoid or glenoid replacement, and said stem having a width of between about 45% and 60% of the width of said head, each of said 4 fins of said cruciform stem, which fins extend radially from a center axial region, having a thickness equal to between about 2 mm and 3 mm and joining said distal surface of said head at a fillet having a radius of between about 1.5 mm and 2.2 mm.

DETAILED DESCRIPTION OF THE PREFERRED EMBODIMENTS

Very careful engineering and innovation was required to design a pyrolytic carbon-graphite humeral head resurfacing implant that will meet the strength and performance requirements of such a prosthesis while still conserving bone, which is a prime objective of any such resurfacing implant.

Figure 1:
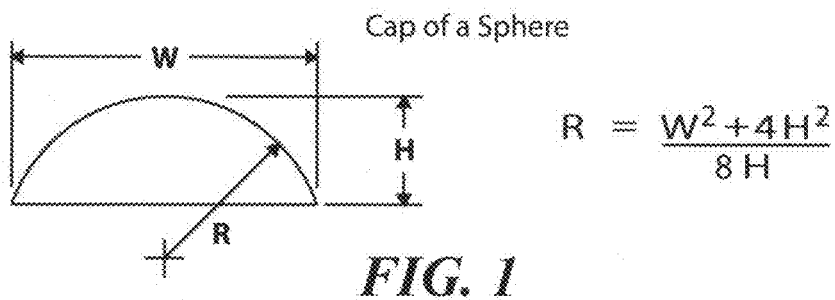
FIG. 1 is an illustration of a cap of a sphere.

Assuming the articular portion of the humeral head is spherical, its articular outer surface can be described as generally that of a spherical cap having the characteristic dimensions of height (H), radius of curvature (R) and width (W) as illustrated in FIG. 1.

The assumption that the humeral head is spherical is only partially accurate because the native humeral head is actually slightly oval-shaped, with its base width in the anterior/posterior direction being about ninety-two percent of the width in the superior/inferior direction. However, from an overall consideration standpoint, considering the humeral head to be a segment of a sphere is a reasonable assumption, and the head portion of the humeral head resurfacing implant described herein preferably has an articulation surface that is a spherical cap. The mathematical relationship between H, W and R for a cap of a sphere is shown in FIG. 1. Knowledge of any two of the variables (W, H, or R) allows for calculation of the third.

The biomechanical forces associated with shoulder joint function will determine the load-bearing requirement for a humeral head resurfacing implant. ASTM F 1378 05, Standard Specification for Shoulder Prostheses, states the worse joint load acting on a humeral head can be 2 times body weight. Assuming a body weight of 190 lbs., the magnitude of the joint force acting on the humeral head would be approximately 380 lbs. The direction of the joint force will depend on the posture of the arm and the activity being performed. The force acting on the humeral head will have components acting in both the axial direction and the lateral direction. Biomechanical analysis determined that the direction of the joint force is inclined to the humeral head at an angle of approximately 30 degrees for the worse case joint load of two times body weight.

Stem Design Considerations

The implant designer should consider two factors when designing the implant stem 1) the stem must be strong and durable enough to withstand the biomechanical forces encountered, and 2) fixation of the stem to bone must be sufficient to withstand the biomechanical forces encountered. Stem strength is a function of the stem cross sectional geometry, and fixation to bone strength is a function of stem surface area.

The thickness and radial extension of fins in a stem of cruciform cross-section are most important. A finned stem of careful design can offer the following advantages:

1. Stem fin configuration provides a large surface area to insure primary and long term fixation of the implant to bone.

2. Stem fin configuration provides a large radial projected surface area to improve resistance to lateral rotation of the implant.

3. Stem fin configuration provides a large, radial-projected surface area to improved resistance to axial rotation of the implant.

4. Stem fin configuration provides for radial extension of the fins allowing the fins to engage denser and stronger peripheral cancellous bone.

5. Stem fin configuration results in enhanced overall stem strength.

6. Stem fin configuration provides high stem surface area to volume ratio that minimizes bone removal and enhances bone fixation.

Cancellous Bone Structure of Humeral Head

The head and neck portion of the humerus consists of an outer layer of cortical bone and an inner volume of cancellous bone. Cancellous bone is a highly porous or cellular form of bone. The stem of a resurfacing implant will reside in the cancellous bone structure. Cancellous bone is porous latticework of bony bars and plates where the volume traction of bone material can range from 5% to 70%. The interstices (void spaces) of cancellous bone are filled with marrow. The mechanical strength of cancellous bone is less than dense cortical bone, and the strength of cancellous bone decreases as its porosity increases. The density of cancellous bone varies with location. The cancellous bone near the centerline of the humeral neck is often of low density, and its density increases from the centerline to the periphery. This is especially the case in individuals suffering from arthritis and or osteoporosis where the strength of the bone in the center of the humeral head can be very poor. Because the cancellous bone in the central portion of the humeral head has lower density and lower strength, it is advantageous to have the stem fins extend significantly radially out from the bone centerline to denser and stronger peripheral cancellous bone.

Figure 2:
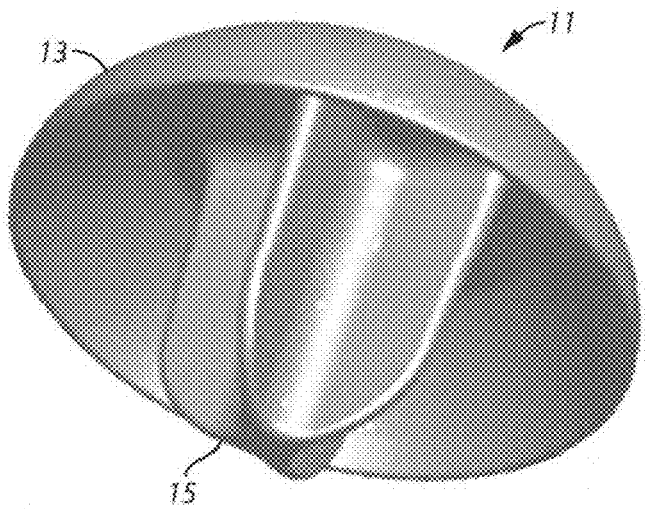
FIG. 2 is a perspective view of a humeral head resurfacing implant embodying various features of the present invention.

FIG. 2 illustrates a humeral head resurfacing implant 11 embodying various features of the present invention. Its design allows it to be manufactured from a substrate of isotropic graphite, which has previously been used for the production of prosthetic implants of substantial thickness. The substrate is completely covered with a layer of dense, isotropic pyrocarbon of carefully selected physical properties, which pyrocarbon layer adds significant structural strength to the underlying isotropic graphite substrate. The marriage of these two materials and the careful design of the head of the implant and the cruciform stem, and particularly the region where the stem meets the head, combine to allow the production of an integral implant that embodies the desired surface properties of pyrocarbon and an overall modulus of elasticity close to that of human bone.

The humeral head resurfacing implant 11 shown in FIG. 2 is manufactured from a machined substrate of dense isotropic graphite which is then coated substantially completely overall with a layer of dense, pyrolytic carbon. This particular combination of materials facilitates the production of such a humeral head resurfacing implant having a modulus of elasticity very close to that of human cortical bone. The relative brittleness of these construction materials is overcome by careful engineering design that results in a structure which requires only minimal removal of bone while still providing an implant with strength such as to allow implantation without damage and assure long-lasting service and wear for the life of the patient, barring unusual circumstances.

The machined graphite substrate is formed from dense, isotropic, fine-grain graphite, such as Poco AXF-5Q Biomedical Grade Graphite having a density greater than about 1.75 gm/cm$^3$. Preferably, the entire exterior surface of the machined substrate is covered with a layer of dense pyrolytic carbon, which is chosen for its ability to exhibit high strength, high wear resistance, biocompatibility, a modulus of elasticity similar to that of cortical bone, an ability to support bone apposition and low friction on polished surfaces. Pyrolytic carbon which is isotropic and which has a density between about 1.7 and about 2.1 gm/cm$^3$ and a hardness of at least about 200 DPH is employed; such carbon sold under the trademark Pyrolite may be used. However, the preferred carbon is unalloyed pyrocarbon made in accordance with the teachings of U.S. Pat. No. 5,677,061, which is commercially available as On-X pyrocarbon. Such unalloyed pyrocarbon can be obtained having a modulus of rupture of at least about 58 ksi, and pyrocarbon having such properties may be preferred as being particularly advantageous for a humeral head resurfacing implant which will be subject to mechanical stresses both during implantation and during life in the shoulder region of the patient.

Such dense pyrocarbon is both stiffer and more fracture-resistant than the underlying machined graphite substrate, and as a result of the high-temperature pyrolytic coating process, it becomes adhered strongly to the exterior surface of the isotropic graphite substrate. The result is one of mechanical reinforcement that provides strength to the composite structure and results in an integral implant exhibiting an elasticity modulus very close to that of human cortical bone, which is considered to be about 23 gigapascals (GPa). To achieve this mechanical reinforcement and provide the desired composite modulus of elasticity, the layer of dense isotropic pyrolytic carbon with which the substrate is coated must have a thickness of at least about 0.20 mm (0.008 in.). Preferably, a substantially uniform layer of unalloyed pyrocarbon having a thickness between about 0.25 mm (0.01 in) and about 0.75 mm (0.03 in) is employed and can provide an elastic modulus within about 25% of that cortical bone.

The implant 11 includes an integral head 13 and stem 15 that is formed by the integral isotropic graphite substrate that is then coated with a layer of dense pyrocarbon over substantially its entire surface. The graphite substrate has a head section in the form of a section of a spheroid and a stem portion which extends from the undersurface or distal surface of the head portion. The coated substrate thus provides a convex articular surface 17 in the form of a section of a spheroid, preferably that of a cap of a sphere, which forms the proximal surface of the implant that will be polished and will interface with a patient's glenoid or a with a patient's glenoid replacement should the native glenoid require such replacement. Although the head 13 would function so long as it was of a suitable spheroidal shape, for manufacturing and implantation purposes, a spherical shape is preferably chosen. The head 13 includes a cap portion 19, that may be the solid cap of a sphere (FIG. 1) as illustrated in FIG. 6, and an integral, depending peripheral skirt portion 21, which is relatively thin and, in the orientation depicted in FIGS. 2, 3 and 6, depends below the distal surface of the cap 19 by the amount J (FIG. 6). The skirt 21 has an interior surface 22 that is preferably a concave section of a spherical surface that is slightly bulbous at its peripheral edge. The undersurface or distal surface of the solid cap portion, as best seen in FIGS. 3, 5 and 6, is a flat surface 23, and the stem 15 extends from the precise center of the circular flat surface 23.

Figure 3:
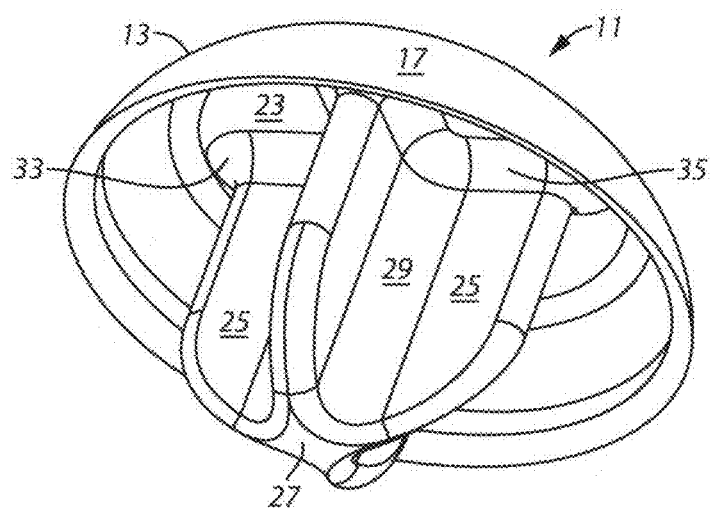
FIG. 3 is a line drawing similar to FIG. 2.
Figure 4:
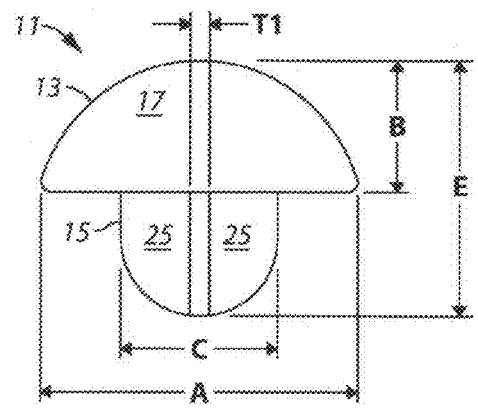
FIG. 4 is a front view of the implant of FIG. 2
Figure 5:
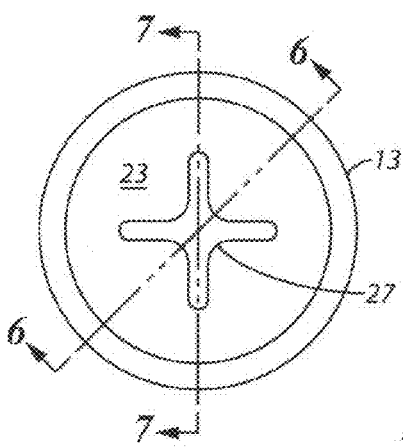
FIG. 5 is a bottom view of the implant of FIG. 2.
Figure 7:
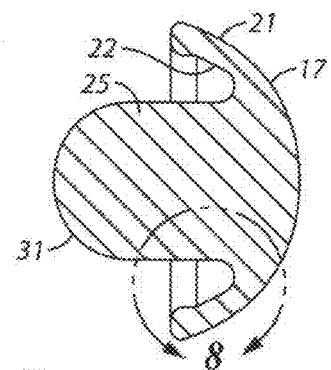
FIG. 7 is a sectional view taken along the line 7-7 of FIG. 5.
Figure 6:
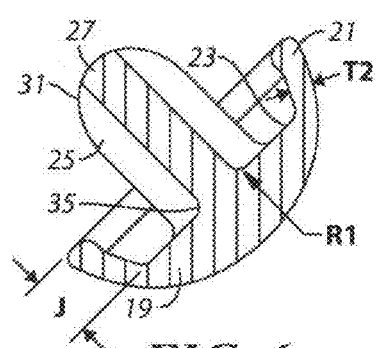
FIG. 6 is a sectional view taken along the line 6-6 of FIG. 5.

The stem 15 has a cruciform cross section with four fins 25 aligned at right angles to one another and extending radially outward from a central axial region 27 as seen in FIGS. 3 and 5. The central axial region 27 has a thickness greater than any one of the four fins 25, which are of equal thickness (T1) (FIG. 4), and it includes four curved web regions 29 that are respectively located between each pair of adjacent fins as best seen in FIGS. 3 and 5. The distal tip or end 31 of the stem (FIG. 7) is curved so as to facilitate entry into the cancellous bone region of the humerus head which has been prepared, and the fins may 25 be tapered longitudinally by few degrees to effect a tight press-fit. To secure long-lasting implantation, it is important that an excessive amount of bone not be reamed or removed from the humerus when a humeral head resurfacing implant is used. Accordingly, the implant 11 is designed to have a thin skirt region 21 that limits the amount of bone that must be shaved or reamed from the surface of the humeral head that faces the glenoid. Most importantly, the stem 15 is proportioned and designed to minimize the amount of bone that will need to be removed from the humerus while still providing adequate overall mechanical strength and an overall elastic modulus very close to that of human bone; it provides surface area sufficient to facilitate bone adhesion and secure long-term incorporation into the head of the humerus. To achieve these ends, it was necessary to very carefully engineer the implant 11 to arrive at an integral, pyrocarbon-coated graphite substrate that would have these attributes and a modulus of elasticity essentially that of human cortical bone.

It is well known that it will be necessary to produce such implants in a variety of sizes so that a surgeon at the time of implantation can choose the size that is anatomically the best fit for the repair of the shoulder of a particular patient, and as indicated hereinbefore, it is likely that one would wish to produce these implants having head width sizes between about 38 mm and about 56 mm. Generally, for implants of such size, the radius of curvature of the spherical head will range between about 18 mm and 29 mm. It is important that the size of the stem is made proportional to the width of the head and particularly to structurally blend and merge with the interior surface of the skirt 21. The width of the head 13 is labeled (A) in FIG. 4, and the width of the stem 15 is measured lateral edge to lateral edge of 2 coplanar fins and is labeled (C). It has been determined that the stem 15 should have a width within between about 45% and 60% of the width (A) of the head to assure adequate support for the head of the resurfacing implant and preferably between about 45% and 50%. If the stem is so proportioned for an implant having a skirt with a thickness T2 (FIG. 6) of about 2-3 mm, the interior region of the head can be sized so that the radial edges of the fins of the stem are located so they can carefully transition to the interior surface of the skirt where a fillet or radius of curvature 33 is established therebetween (see FIG. 8) which measures between 1.5 mm and 2.2 mm, and preferably between about 2.0 and 2.2 mm.

Such has proved to be a very important criterion for an implant made from these particular materials; however the radius of curvature or fillet 35 at the location where the fins 25 of the stem join the flat undersurface 23 of the cap portion 19 of the head, which is referred to as the distal surface, is likewise important. It has been found that by maintaining such fillets 33 and 35 within a very narrow range of radius of curvature, a strong yet acceptable implant is obtained. It is preferred that radii R1 and R2 be both sized between 2.0 mm and 2.2 mm; more preferably, a radius of 2.1 mm plus or minus 0.03 mm is used to achieve the aforestated objectives. From the standpoint of resisting potential fracture while minimizing bone removal, the radii of curvature of the fillets 33 and 35 between the fins 25 and either the flat distal surface 23 or the interior surface of the skirt portion 21 are of importance.

Figure 8:
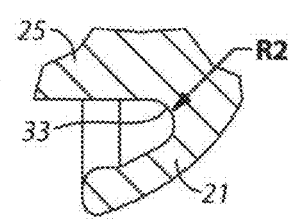
FIG. 8 is an enlarged fragmentary sectional view showing the encircled portion of FIG. 7.

The thickness T2 (FIG. 6) of the skirt, i.e. the distance between the spherical surfaces 17 and 22, may vary slightly as implants range in size from the smallest at a 38 mm head width and the largest at a 56 mm head width; for example, T2 may be as thin as about 2 mm (0.08 in) for the smallest size head, but it preferably varies between about 2.4 mm (0.095 in) and 3.0 mm (0.120 in). More preferably, the thickness T2 is maintained between about 2.5 mm (0.098 in) and about 2.7 mm (0.105 in), and most preferably between about 2.5 mm (0.098 in) and 2.6 mm (0.102 in). The skirt may terminate in a slightly bulbous peripheral or terminal region as seen in FIGS. 6 and 8. Careful engineering allows such a pyrocarbon/graphite implant to provide necessary strength yet require only minimal bone removal that is a hallmark of a humeral head resurfacing implant.

As mentioned before, each of the four fins 25 extends radially from the central axial region 27 of the stem, which region is best seen in FIGS. 5 and 6. The fins 25 are proportioned to the width of the head 13 so that the stem 15 will be adequately supporting and afford the aforementioned important transition between the lateral or radial edges of the fins and the interior surface of the skirt. The fins should have a thickness (T1) between about 2 mm (0.08 in) and about 3 mm (0.12 in) and preferably between about 2 mm and 2.5 mm (0.1 in). It has also been found important that the radial width of each fin, i.e. the distance between the lateral edge of the fin 25 and the central axial region 21, should be between about 20% to 30% of the head width, and preferably between about 20% and 25% of the head width. This arrangement limits the central axial region 27 to an acceptable volume while providing adequate strength.

Overall, the head 13, which includes the skirt region 21, should not have a height (dimension B) that exceeds about 65% of the height (dimension E) of the overall implant 11. In the FIGS. 4 and 6 embodiment, the height of the skirt 21, identified by the reference J in FIG. 6, is equal to about 45 to 65% of the height B of the head 13, and there is also an important relationship between the height B of the head and the radius R (FIG. 1) of the sphere. The height B of the head should always be less than the radius of the spherical surface 17, i.e. the radius of the spherical cap; thus, the articular surface 19 of the implant will be less than that of a hemisphere. Preferably, the head 13 will be proportioned to have a height B equal to about 55% and about 90% of the radius of the sphere and more preferably between 65% and 90%. As mentioned before, in the FIGS. 2 and 3 embodiment, the head 13 is a composite of a spherical cap portion 19 and a depending skirt portion 21.

By engineering to the criteria set forth hereinabove, a one-piece, integral humeral head resurfacing implant or prosthesis can be created by depositing dense pyrocarbon of particular physical parameters onto an isotropic graphite substrate. Although both pyrocarbon and graphite are brittle materials, careful restriction to these criteria permits the design of a implant with sufficient strength and durability to withstand expected service conditions while taking into consideration certain pertinent factors that need not be considered when one designs implants of strong Co—Cr alloys or the like. As a result of this careful engineering and proportioning, one is able to obtain a humeral head resurfacing implant that, while exhibiting most desirable biological compatibility to bone and tissue, i.e. particularly a modulus of elasticity close to that of human cortical bone, also exhibits satisfactory biomechanical loading and impact resistance during surgical insertion, together with strength and fracture resistance throughout an extended service lifetime.

Although various preferred embodiments are illustrated and described hereinbefore, it should be understood that changes and modifications that would be obvious to one having ordinary skill in this art may be added without departing from the scope of the invention. Particular features of the invention are emphasized in the claims which follow.

The invention claimed is:
1. A humeral head resurfacing implant comprising an integral head and stem which implant comprises:
an integral isotropic graphite substrate having a head portion and a distal stem portion,
a coating of isotropic pyrocarbon having a thickness of at least about 0.2 mm that covers substantially said entire substrate, which pyrocarbon has a density of between about 1.7 and 2.1 gm/cm$^3$ and a hardness of at least about 200 DPH,
said head portion of said substrate having an exterior surface shape of a section of a spheroid, which surface serves as a proximal surface to interface with a patient's glenoid or glenoid replacement,
said head portion comprising a solid cap section with an undersurface from which said stem portion extends and a surrounding peripheral skirt section,
said stem portion of said substrate being integral with said cap section of said head portion and having a plurality of flat surfaces, and
each of said flat surfaces of said stem portion being connected to said undersurface of said cap section at a fillet having a radius of between about 1.5 mm and 2.2 mm,
wherein said skirt section has a height (J) that is between about 45% and 65% of a height (B) of said head portion.
2. The humeral head resurfacing implant according to claim 1 wherein said head portion height (B) is about 45% to 65% of a height (E) of the substrate.

3. The humeral head resurfacing implant according to claim 2 wherein said proximal surface of said head portion is spherical having a radius of between about 18 mm and 29 mm.

4. The humeral head resurfacing implant according to claim 3 wherein said skirt section has a thickness of between about 2 mm and 3 mm.

5. The humeral head resurfacing implant according to claim 4 wherein said skirt section has a thickness between about 2.5 mm and about 2.7 mm.

6. The humeral head resurfacing implant according to claim 5 wherein said skirt section terminates in a bulbous peripheral edge.

7. The humeral head resurfacing implant according to claim 1 wherein said stem portion comprises a plurality of fins, said plurality of fins comprising the plurality of flat surfaces, which fins individually extend from the axial center of said stem portion, and said fillets being where said plurality of flat surfaces of the fins are connected to said undersurface have a radius of about 2.0 mm to 2.2 mm.

8. The humeral head resurfacing implant according to claim 7 wherein each of said fins has two flat surfaces that are substantially parallel and a radial width equal to between about 20% and 30% of a width (A) of said head portion.

9. The humeral head resurfacing implant according to claim 7 wherein said stem portion of said graphite substrate has fins of an uncoated thickness not less than 1.5 mm.

10. The humeral head resurfacing implant according to claim 9 wherein each of said fins of said stem portion has a thickness (T1) between about 2 mm and about 3 mm.

11. The humeral head resurfacing implant according to claim 10 wherein each of said fins of said stem portion has a thickness (T1) between about 2.0 mm and about 2.5 mm.

12. The humeral head resurfacing implant according to claim 1 wherein said pyrocarbon coating is unalloyed pyrocarbon having a thickness of between about 0.25 mm and 0.75 mm.

13. The humeral head resurfacing implant according to claim 1 wherein said undersurface is flat.

14. The humeral head resurfacing implant according to claim 1 wherein said exterior surface shape of said section of said spheroid is polished.

\* \* \* \* \*